US008571621B2

(12) United States Patent
Stetson et al.

(10) Patent No.: US 8,571,621 B2
(45) Date of Patent: Oct. 29, 2013

(54) MINIMAX FILTERING FOR PULSE OXIMETRY

(75) Inventors: Paul F. Stetson, Piedmont, CA (US); James Ochs, Seattle, WA (US)

(73) Assignee: Covidien LP, Mansfield, MA (US)

( * ) Notice: Subject to any disclaimer, the term of this patent is extended or adjusted under 35 U.S.C. 154(b) by 514 days.

(21) Appl. No.: 12/822,579

(22) Filed: Jun. 24, 2010

(65) Prior Publication Data

US 2011/0071374 A1 Mar. 24, 2011

Related U.S. Application Data

(60) Provisional application No. 61/245,569, filed on Sep. 24, 2009.

(51) Int. Cl.
*A61B 5/00* (2006.01)

(52) U.S. Cl.
USPC .......................................... 600/324

(58) Field of Classification Search
USPC .......................................... 600/324
See application file for complete search history.

(56) References Cited

U.S. PATENT DOCUMENTS

| 3,638,640 A | 2/1972 | Shaw |
| 4,289,141 A | 9/1981 | Cormier |
| 4,936,679 A | 6/1990 | Mersch |
| 4,971,062 A | 11/1990 | Hasebe et al. |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,094,239 A | 3/1992 | Jaeb et al. |
| 5,143,078 A | 9/1992 | Mather et al. |
| 5,275,159 A | 1/1994 | Griebel |
| 5,483,646 A | 1/1996 | Uchikoga |
| 5,730,124 A | 3/1998 | Yamauchi |
| 5,779,631 A | 7/1998 | Chance |
| 5,830,139 A | 11/1998 | Abreu |
| 5,831,598 A | 11/1998 | Kauffert et al. |
| 5,871,442 A | 2/1999 | Madarasz et al. |

(Continued)

FOREIGN PATENT DOCUMENTS

| DE | 69123448 | 5/1997 |
| WO | WO9200513 | 1/1992 |

(Continued)

OTHER PUBLICATIONS

Simon, Dan. "Minimaz Filtering." Minimax Filtering. Innovatia Software, n.d. Web. <http://web.archive.org/web/20090130141627/http://www.innovatia.com/software/papers/minimax.htm>.*

(Continued)

*Primary Examiner* — Clayton E Laballe
*Assistant Examiner* — Dennis Hancock
(74) *Attorney, Agent, or Firm* — Fletcher Yoder PC

(57) ABSTRACT

Methods and systems are provided for filtering a pulse oximetry signal without making assumptions on the noise statistics of the signal. A pulse oximeter may receive an energy signal proportional to an amount of light detected at the sensor. The energy signal may be converted and digitally processed to estimate physiological data. The pulse oximeter may include a processor configured to execute $H_\infty$ filtering algorithms to estimate physiological data without requiring the variances and/or distributions of measurement and process noise in the signal. In one or more embodiments, the pulse oximeter may also be configured to execute other filtering algorithms which update $H_\infty$ filtering algorithms based on the pulse oximetry signal.

19 Claims, 2 Drawing Sheets

(56) References Cited

U.S. PATENT DOCUMENTS

| | | | |
|---|---|---|---|
| 5,873,821 | A | 2/1999 | Chance et al. |
| 5,921,921 | A | 7/1999 | Potratz et al. |
| 6,081,742 | A | 6/2000 | Amano et al. |
| 6,120,460 | A | 9/2000 | Abreu |
| 6,134,460 | A | 10/2000 | Chance |
| 6,163,715 | A | 12/2000 | Larsen et al. |
| 6,285,895 | B1 | 9/2001 | Ristolainen et al. |
| 6,312,393 | B1 | 11/2001 | Abreu |
| 6,353,750 | B1 | 3/2002 | Kimura et al. |
| 6,415,236 | B2 | 7/2002 | Kobayashi et al. |
| 6,419,671 | B1 | 7/2002 | Lemberg |
| 6,461,305 | B1 | 10/2002 | Schnall |
| 6,487,439 | B1 | 11/2002 | Skladnev et al. |
| 6,526,301 | B2 | 2/2003 | Larsen et al. |
| 6,544,193 | B2 | 4/2003 | Abreu |
| 6,549,795 | B1 | 4/2003 | Chance |
| 6,591,122 | B2 | 7/2003 | Schmitt |
| 6,606,509 | B2 | 8/2003 | Schmitt |
| 6,618,042 | B1 | 9/2003 | Powell |
| 6,622,095 | B2 | 9/2003 | Kobayashi et al. |
| 6,662,030 | B2 | 12/2003 | Khalil et al. |
| 6,675,029 | B2 | 1/2004 | Monfre et al. |
| 6,687,519 | B2 | 2/2004 | Steuer et al. |
| 6,690,958 | B1 | 2/2004 | Walker et al. |
| 6,714,245 | B1 | 3/2004 | Ono |
| 6,731,274 | B2 | 5/2004 | Powell |
| 6,785,568 | B2 | 8/2004 | Chance |
| 6,793,654 | B2 | 9/2004 | Lemberg |
| 6,850,053 | B2 | 2/2005 | Daalmans et al. |
| 6,898,451 | B2 | 5/2005 | Wuori |
| 6,949,081 | B1 | 9/2005 | Chance |
| 7,016,715 | B2 | 3/2006 | Stetson |
| 7,035,697 | B1 | 4/2006 | Brown |
| 7,041,063 | B2 | 5/2006 | Abreu |
| 7,043,289 | B2 | 5/2006 | Fine et al. |
| 7,065,392 | B2 | 6/2006 | Kato |
| 7,095,491 | B2 | 8/2006 | Forstner et al. |
| 7,212,847 | B2 | 5/2007 | Petersen et al. |
| 7,236,811 | B2 | 6/2007 | Schmitt |
| 7,239,902 | B2 | 7/2007 | Schmitt et al. |
| 7,272,426 | B2 | 9/2007 | Schmid |
| 7,469,158 | B2 | 12/2008 | Cutler et al. |
| 7,551,950 | B2 | 6/2009 | Cheng |
| 7,621,877 | B2 | 11/2009 | Schnall |
| 2002/0042558 | A1 | 4/2002 | Mendelson |
| 2002/0156354 | A1 | 10/2002 | Larson |
| 2002/0198443 | A1 | 12/2002 | Ting |
| 2003/0023140 | A1 | 1/2003 | Chance |
| 2004/0138538 | A1 | 7/2004 | Stetson |
| 2004/0171920 | A1 | 9/2004 | Mannheimer et al. |
| 2005/0113651 | A1 | 5/2005 | Wood et al. |
| 2005/0113656 | A1 | 5/2005 | Chance |
| 2005/0124871 | A1* | 6/2005 | Baker et al. ............ 600/323 |
| 2005/0143634 | A1* | 6/2005 | Baker et al. ............ 600/310 |
| 2005/0192488 | A1 | 9/2005 | Bryenton et al. |
| 2005/0228248 | A1 | 10/2005 | Dietiker |
| 2006/0020181 | A1 | 1/2006 | Schmitt |
| 2006/0030766 | A1 | 2/2006 | Stetson |
| 2006/0247501 | A1 | 11/2006 | Ali |
| 2007/0208233 | A1 | 9/2007 | Kovacs |

FOREIGN PATENT DOCUMENTS

| | | |
|---|---|---|
| WO | WO9309711 | 5/1993 |
| WO | WO9842249 | 10/1998 |
| WO | WO9842251 | 10/1998 |
| WO | WO0176461 | 10/2001 |
| WO | WO2006109072 | 10/2006 |
| WO | WO2008096241 | 8/2008 |

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Poets, C. F., et al.; "Detection of movement artifact in recorded pulse oximeter saturation," *Eur. J. Pediatr.*; vol. 156, pp. 808-811 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Hayes, Matthew J., et al.; "Artifact reduction in photoplethysmography," *Applied Optics*, vol. 37, No. 31, pp. 7437-7446 (Nov. 1998).

Hayes, Matthew J., et al.; "Quantitative evaluation of photoplethysmographic artifact reduction for pulse oximetry," *SPIE*, vol. 3570, pp. 138-147 (Sep. 1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Kaestle, S.; "An Algorithm for Reliable Processing of Pulse Oximetry Signals Under strong Noise Conditions," *Dissertation Book*, Lubeck University, Germany (1999).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Goldman, Julian M.; "Masimo Signal Extraction Pulse Oximetry," *Journal of Clinical Monitoring and Computing*, vol. 16, pp. 475-483 (2000).

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Kaestle, S.; "Determining Artefact Sensitivity of New Pulse Oximeters in Laboratory Using Signals Obtained from Patient," *Biomedizinische Technik*, vol. 45 (2000).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

(56) References Cited

OTHER PUBLICATIONS

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie.*

Hamilton, Patrick S., et al.; "Effect of Adaptive Motion-Artifact Reduction on QRS Detection," *Biomedical Instrumentation & Technology*, pp. 197-202 (undated).

P. Lang, et al.; "Signal Identification and Quality Indicator™ for Motion Resistant Pulse Oximetry," *Abstracts*, A10, p. S105. (undated).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

MINIMAX FILTERING FOR PULSE OXIMETRY

RELATED APPLICATION

This application claims the benefit of U.S. Provisional Application No. 61/245,569, filed Sep. 24, 2009, which application is hereby incorporated by reference.

BACKGROUND

The present disclosure relates generally pulse oximetry and, more particularly, to processing of pulse oximetry data.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Certain filtering techniques may be implemented with the various algorithms to estimate the amount of blood constituent in the tissue. Filters may reduce errors in estimating the blood constituent in tissue by removing noise from the data. For example, the data, which may include the received signal of light absorption and/or scattering by the tissue, may also include non-physiological components resulting from interferences in the pulse oximetry system. Current pulse oximeters generally use Kalman filtering, which may minimize the mean square error of estimation. However, Kalman filters typically assume a stationary zero-mean uncorrelated noise distribution. Noise in a pulse oximetry system may sometimes deviate from the Kalman filtering noise assumptions, resulting in estimation errors in filtering pulse oximetry data.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present techniques relate to methods of filtering a signal to estimate one or more physiological parameters relating to pulse oximetry. More specifically, present techniques are directed to "minimax filters," also referred to as "$H_\infty$ filters," which are derived to minimize the maximum error of a pulse oximetry signal due to any possible disturbance, without making assumptions about the interferences in the system. For example, physiological data such as blood-oxygen saturation of hemoglobin in arterial blood, the volume of individual blood pulsations supplying the tissue, the rate of blood pulsations corresponding to each heartbeat of a patient, and/or the average shape of a plethysmographic waveform may be estimated from a pulse oximetry signal.

A typical filter used in pulse oximetry estimations, such as a Kalman filter, may be derived to minimize an average error of estimation, and may make assumptions about interferences in the system. A Kalman filter may include algorithms which use stationary and zero-mean noise distributions and a priori knowledge of noise variances to filter a pulse oximetry signal. However, a Kalman filter may not be completed, and may not be effective, if interference or measurement errors in the pulse oximetry system cause the noise distributions to deviate from an average noise distribution used in the Kalman filter. Furthermore, in some pulse oximetry systems, the statistics of noise sources may not be fully known or available, and may not be fed into the Kalman filter algorithms.

As will be explained, present techniques of filtering a pulse oximetry signal may be directed towards minimizing the maximum error due to any possible disturbance in a pulse oximetry signal, thus minimizing the worst case estimation error. Further, the filtering methods may be derived without making assumptions about interferences in the pulse oximetry system. Filters, and methods of filtering the pulse oximetry signals, may be more robust and capable of improved estimations of physiological data from pulse oximetry signals affected by noise sources with unknown or less predictable statistics.

Figure 1:
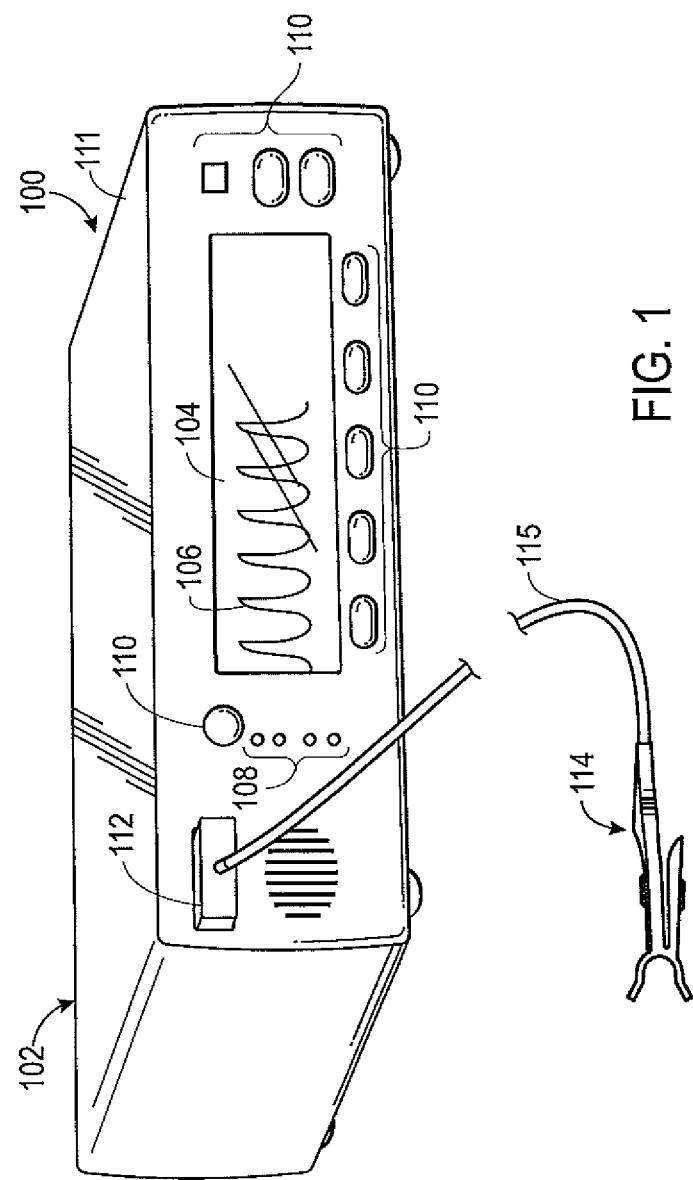
FIG. 1 illustrates a perspective view of a pulse oximeter in accordance with an embodiment.

Now turning to the figures, FIG. 1 is a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
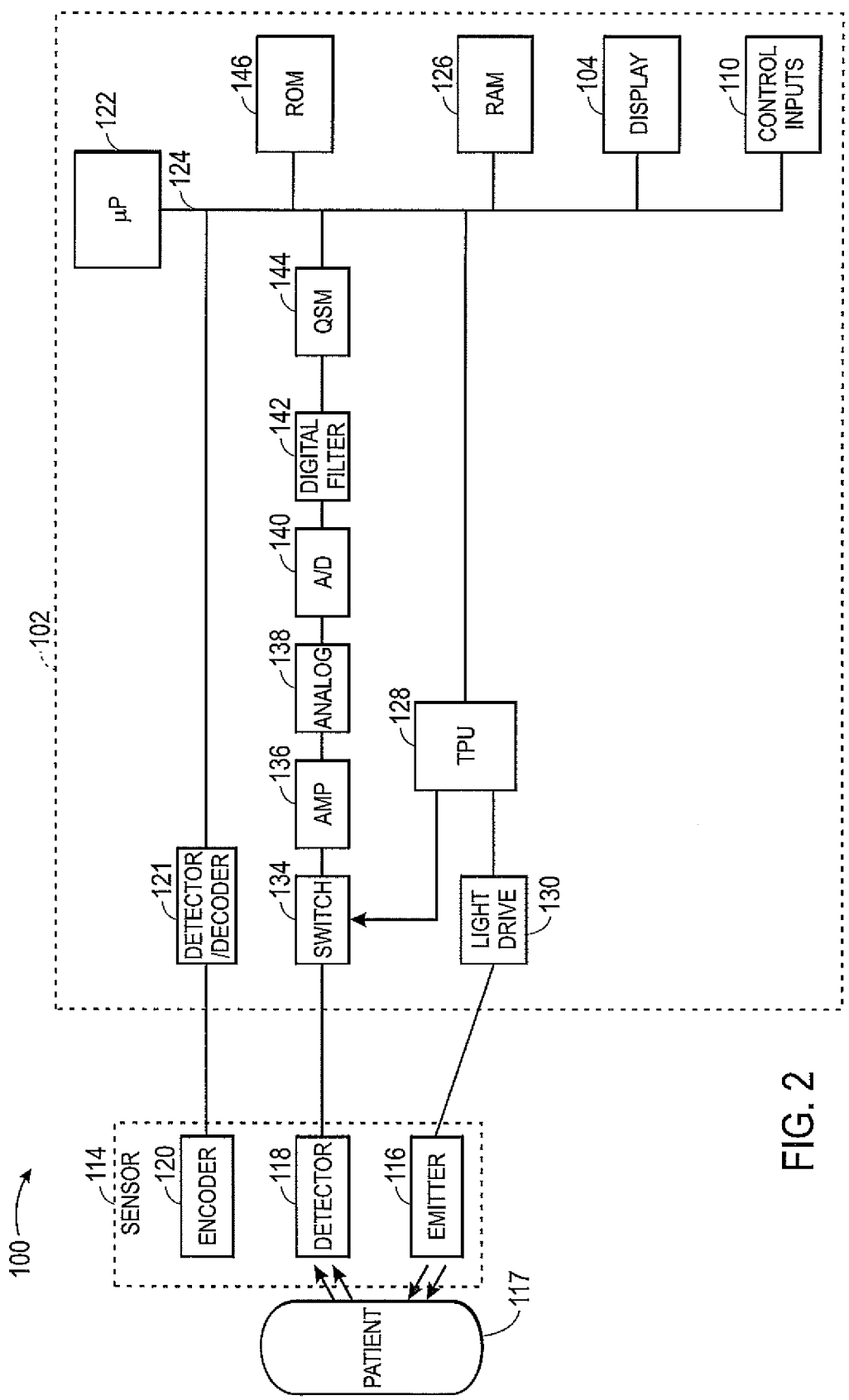
FIG. 2 illustrates a simplified block diagram of a pulse oximeter in FIG. 1, according to an embodiment.

Turning to FIG. 2, a simplified block diagram of a pulse oximeter 100 is illustrated in accordance with an embodiment. Specifically, certain components of the sensor 114 and the monitor 102 are illustrated in FIG. 2. The sensor 114 may include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 nm. The emitter 116 may include a single emitting device, for example, with two light emitting diodes (LEDs) or the emitter 116 may include a plurality of emitting devices with, for example, multiple LED's at various locations. Regardless of the number of emitting devices, the emitter 116 may be used to measure, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 118 may be an array of detector elements that may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. After converting the received light to an electrical signal, the detector 118 may send the signal to the monitor 102, where physiological characteristics may be calculated based at least in part on the absorption of light in the tissue of the patient 117. As used herein, the electrical signal converted from the received light may also be referred to as a pulse oximetry signal.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients or to derive a filter for estimating the patient's physiological characteristics. The encoder 120 may, for instance, be a memory on which one or more of the following information may be stored for communication to the monitor 102: the type of the sensor 114; the wavelengths of light emitted by the emitter 116; variances associated with sources of interferences; and the proper calibration coefficients and/or algorithms to be used for calculating the patient's 117 physiological characteristics. For example, in one embodiment, a filter 142 in the monitor 102 may use the variances associated with sources of interferences to adaptively filter a pulse oximetry signal. Further, in some embodiments, the data or signal from the encoder 120 may be decoded by a detector/decoder 121 in the monitor 102.

Signals from the detector 118 and the encoder 120 may be transmitted to the monitor 102. The monitor 102 may include one or more processors 122 coupled to an internal bus 124. Also connected to the bus may be a RAM memory 126 and a display 104. A time processing unit (TPU) 128 may provide timing control signals to light drive circuitry 130, which controls when the emitter 116 is activated, and if multiple light sources are used, the multiplexed timing for the different light sources. TPU 128 may also control the gating-in of signals from detector 118 through an amplifier 132 and a switching circuit 134. These signals are sampled at the proper time, depending at least in part upon which of multiple light sources is activated, if multiple light sources are used. The received signal from the detector 118 may be passed through an amplifier 136, an analog filter 138, and an analog-to-digital (A/D) converter 140, and/or a digital filter 142 for amplifying, filtering, digitizing, and/or processing the electrical signals from the sensor 114.

The analog filter 138 may be used to remove unwanted frequency components from the signals and/or enhance desired components of the signal, and may include any combination of electronic filters (e.g., low pass filters, high pass filters, band pass filters, etc.). The digital filter 142 may further be used to remove unwanted frequency components from the digitized signal and/or enhance desired components of the signal. The digital filter 142 may comprise a microprocessor configured to access and apply algorithms for digital signal processing. For example, the algorithms may include $H_\infty$ filter algorithms. In some embodiments, the A/D converter 140 may either be a part of, or separate from and coupled to, the digital filter 142. After, amplifying, filtering, digitizing, and/or processing, the digital data may then be stored in a queued serial module (QSM) 144, for later downloading to RAM 126 as QSM 144 fills up. In an embodiment, there may be multiple parallel paths for separate amplifiers, filters, and A/D converters for multiple light wavelengths or spectra received.

In an embodiment, based at least in part upon the received signals corresponding to the light received by detector 118, processor 122 may determine various physiological data, such as oxygen saturation level, blood pulse rate, etc. In determining the physiological data, the processor 122 may use various algorithms to calculate, identify, and/or characterize the physiological data from the received signal. These algorithms may require coefficients, which may be empirically determined. For example, algorithms relating to the distance between an emitter 116 and various detector elements in a detector 118 may be stored in a ROM 146 and accessed and operated according to processor 122 instructions. Furthermore, determining the physiological data may also involve signal processing, as discussed above, to enhance a pulse oximetry signal by filtering noise. The noise in the received signal may result from interferences in the pulse oximeter 100 or the between the sensor 114 and the patient 117, for example. In one or more embodiments, the digital filter 142 may be a part of the processor 122, and the processor 122 may also access the ROM 146 for coefficients to be used in digital filtering and other signal processing. Thus, the received signal may be digitized (e.g., by the A/D converter 140 or the digital filter 142) and processed (e.g., by the processor 122), which may include filtering (e.g., by the processor 122 and/or the digital filter 142) the digitized signal to minimize estimation errors.

Certain filtering techniques may be used in a pulse oximeter 100 to minimize estimation errors. For example, some pulse oximeters involve adaptive filtering, which may include adjusting a transfer function such that the filter may be variable (i.e., adaptable) based on the input signal. One type of adaptive filtering used in a typical pulse oximeter may be Kalman filtering. The Kalman filter may be a type of adaptive filter which minimizes the mean square error of the estimation.

To better compare Kalman filtering with the filtering methods of the present techniques, Kalman filters will be explained in further detail. A Kalman filter generally uses a priori knowledge of noise statistics to solve the following linear system:

$$x_{k+1} = Ax_k + Bu_k + w_k \qquad \text{equation (1)}$$

$$y_k = Cx_k + z_k \qquad \text{equation (2)}$$

In equation (1) $x_k$ and $x_{k+1}$ are the system state at time k and k+1, respectively. Using pulse oximetry as an example, the state (x) may represent the value of single digitized plethysmograph sample, a metric related to physiological pulse shape, hemoglobin oxygen saturation measurement (SpO$_2$), pulse rate, or any other signal which may be an input, an output, or an intermediate calculation within an oximetry system. The variable $u_k$ is the known input, or known state change, at time k, and $w_k$ represents the process noise, or the system error, at time k. The matrices A and B in equation (1) selected by the designer and are specific to the system being modeled.

In equation (2) $y_k$ is the measured system output at time k. As seen in equation (2) the measured system output at time k is function of the system state $x_k$ and the measurement error $z_k$. Thus, the matrix C in equation (2) may be specific to the system being modeled.

The system state (x) may be an unknown variable that cannot be measured directly and may need to be estimated. The Kalman filter estimates the state (x) using the system output (y), the previous state estimate (i.e., the previous filter output), and statistical characteristics of the measurement and process error (z and w, respectively). The Kalman filter accomplishes this using the following set of three equations:

$$K_k = AP_k C^T (CP_k C^T + S_z)^{-1} \qquad \text{equation (3)}$$

$$\hat{x}_{k+1} = (A\hat{x}_k + Bu_k) + K_k(y_{k+1} - C\hat{x}_k) \qquad \text{equation (4)}$$

$$P_{k+1} = AP_k A^T + S_w - AP_k C^T S_z^{-1} CP_k A^T \qquad \text{equation (5)}$$

As seen in equation (4), the variable $\hat{x}$ is the state estimate at time k+1. To determine the state estimate $\hat{x}_{k+1}$, the Kalman filters uses two terms. The first term, $A\hat{x}_k + Bu_k$, is the state estimate of the signal if no measurement is taken. The second term, $K_k(y_{k+1} - C\hat{x}_k)$, is a correction term which accounts for the measurement of the input signal, and represents the amount by which to correct the propagated state estimate due to noise introduced in the measurement. The correction term of equation (4) includes the $K_k$ matrix, also called the Kalman gain, which is represented in equation (3). The variable $S_z$ in equation (3), inversely proportional to the Kalman gain, is the covariance matrix of measurement noise (i.e., noise introduced to the output signal $y_{k+1}$). The variable $P_{k+1}$ in equation (3) is the estimation error covariance, and may be computed by equation (5), which includes both the covariance matrix of measurement noise $S_z$ the covariance matrix of process noise $S_w$, and the previous estimation error variance $P_k$. Thus, the covariance matrices of process noise and measurement noise ($S_w$, in equation (5) and $S_z$ in equations (3) and (5)) are both parameters of the Kalman filter equations and used to determine the state estimate $\hat{x}$ in equation (4). This means that if the standard deviation of the noise processes are not known, then $S_w$ and $S_z$ are not known, and an appropriate Kalman filter may not be designed.

Furthermore, the Kalman filter equations also assume that the noise processes are zero mean, which means that the average values of the process noise $w_k$ and the measurement noise $z_k$ must be zero across the duration of the process, and also at each time instant. More specifically, according to the zero mean property of the Kalman filter, the expected values of process noise $w_k$ and measurement noise $z_k$ are zero throughout the process time, and at each instant of the process time.

In some systems, process noise and measurement noise may be unknown. For example, no information may be known regarding noise statistics or system specifications. Furthermore, the process and measurement noises may not always have an average value of zero. In such scenarios when the standard deviation of the noise processes are not know or when noise processes are not zero mean, the inputs for the Kalman filter algorithm may not be available, and the Kalman filter may be incomplete and/or ineffective.

One or more embodiments of the present techniques include filtering techniques which may be used on a pulse oximetry signal when noise statistics may be unknown. The present techniques may also be applicable for noise processes that are not zero mean. More specifically, adaptive filtering such as $H_\infty$ filtering may make no assumptions about noise processes, and may minimize a worst case estimation error. The $H_\infty$ equations may be explained by the equations below:

$$L_k = (I - \gamma Q P_k + C^T V^{-1} C P_k)^{-1} \qquad \text{equation (6)}$$

$$K_k = A P_k L_k C^T V^{-1} \qquad \text{equation (7)}$$

$$\hat{x}_{k+1} = A\hat{x}_k + Bu_k + K_k(y_k - C\hat{x}_k) \qquad \text{equation (8)}$$

$$P_{k+1} = A P_k L_k A^T + W \qquad \text{equation (9)}$$

The state estimate equation (8) may be similar to the state estimate equation from the Kalman filter algorithms, previously presented in equation (4). However, with the $H_\infty$ filter equations, unlike the Kalman filter equations, the covariance of measurement noise $S_z$ and the covariance of process noise $S_w$ are not needed to design the $H_\infty$ filter. To determine the state estimate $\hat{x}_{k+1}$ in equation (8), the $H_\infty$ filter also uses $A\hat{x}_k + Bu_k$, which is the state estimate of the signal if no measurement is taken. Further, the correction term $K_k(y_{k+1} - C\hat{x}_k)$ accounts for the measurement of the input signal, and represents the amount by which to correct the propagated state estimate due to noise introduced in the measurement.

In designing the $H_\infty$ filter, variables of the in the $H_\infty$ filter algorithms may be selected during a design stage of the filter. For example, the variables Q, V, and W are weighting matrices, which may be programmed at the designing stage of the $H_\infty$ filter. The initial values for $\hat{x}_k$ and $P_k$ may also be programmed at the design stage. The parameter $\gamma$ may also be selected during the design stage to set a bound on the worst case estimation error, where the worst case error is equal to $1/\gamma$. The parameter $\gamma$ must be selected such that the eigenvalues of $P_k$ are less then 1, otherwise the solution to the $H_\infty$ filter may not exist.

Furthermore, the programmed variables of the $H_\infty$ filter may also depend on different parameters which may be specific to the system which is measuring and/or filtering the signal, Using a pulse oximetry system as an example, the programmed variables may depend on parameters which may affect the pulse oximetry signal or noise contributing to the signal. For example, characteristics of the pulse oximeter 100, including the sensor 114 and/or the monitor 102, the site of signal measurement (e.g., the finger, forehead, etc.), and the type of physiological data to be estimated may use different programmed variables in the $H_\infty$ filter algorithms. Thus, as can be seen from equations (6), (7), and (9), the calculations for $L_k$, $K_k$, and $P_k$ may be performed off line, and the measurements for $L_k$ and $P_k$ are not needed to compute the $H_\infty$ gain matrix $K_k$. The gain matrix $K_k$ can be computed at some point before running the $H_\infty$ filter (e.g., in a development system), and then hard-coded into an embedded system. Multiple gain matrices $K_k$ may be computed in a development system and stored on the embedded system. The appropriate gain matrix may then be selected at run time depending on the system configuration and/or operating parameters. For example, in a pulse oximetry system, there may be different gain matrices for each pulse oximetry sensor type. The gain matrix may be stored within the sensor 114 itself.

In one or more of the present techniques, $H_\infty$ filtering may be adapted for filtering a signal in a pulse oximeter 100. As discussed, light emitted from the emitter 116 may the detector 118 after passing through the tissue of the patient 117. The detected light may have a certain intensity, which may be directly related to the absorbance and/or reflectance of light in the tissue of the patient 117, and the detector 118 may convert the detected light, based on the intensity, into an electrical signal. The signal output by the detector 118 may include noises from a variety of sources. For example, variations in the sensor 114 such as emitting pulses that are either too strong or too weak, pulses that contain either too much or too little infrared light (or too much or too little red light), pulses that contain waveform artifacts, or pulses that include a high signal-to-noise ratio may all contribute to noise in the signal. Variations in the condition of the patient 117, such as body temperature, dysfunctional hemoglobin, arterial dyes, low perfusion, dark pigment, and/or externally applied coloring agents (such as nail polish or creams which may interfere with a pulse oximeter 100) may also contribute to signal noise. Such noise sources in measuring a pulse oximetry signal with a pulse oximeter 100 may not follow the zero-mean uncorrelated (e.g., Gaussian) noise distributions assumed by Kalman filters. Thus, signal processing in a pulse oximeter 100 may benefit from $H_\infty$ filtering.

The equations below may be used to model the pulsatile waveform (i.e. a plethysmograph) collected by a pulse oximetry system.

$$x_{k+1} = x_k + w_k \qquad \text{equation (10)}$$

$$y_k = x_k + z_k \qquad \text{equation (11)}$$

where the variable $x_k$ is a sample of the actual (unknown) pulse waveform. The actual pulse waveform $x_k$ may change based on normal beat-to-beat variation due to the heart beat of the patient 117, represented by $w_k$ in equation (10). The measured pulse waveform, indicated by $y_k$ in equation (11) includes both the actual waveform $x_k$ and the measurement noise $z_k$, which represents noise and interference in measuring detecting the transmitted light.

A digital filter 142 may include a processor (e.g., microprocessor 122) configured to execute filtering algorithms adapted from $H_\infty$ filters. Applying $H_\infty$ filtering may remove unwanted frequency components corresponding to noise from the signal. The $H_\infty$ filter equations may be adapted depending on the pulse oximetry signal and/or the configuration of the pulse oximeter 100 in which the filter 142 is implemented. For example, different variables, and different weighting matrices may be used to design $H_\infty$ filters for pulse oximeters 100 having different characteristics (e.g., size of the sensors, types of emitters 116 or detectors 118, location of pulse oximetry measurement, etc.). Further, the $H_\infty$ filter equations may be adapted for certain applications, such for estimating different physiological data from a pulse oximetry signal (e.g., oxygen saturation, pulse rate, etc.). Applying the general $H_\infty$ equations (6)-(9) to the 1 dimensional pulse oximetry system model defined by equations (10) and (11), yields the equations (12)-(14) below. These equations are an example of how $H_\infty$ filtering, or any other type of filtering which does not require noise statistics and zero-mean noise distributions, may be adapted to estimate physiological data from a pulse oximetry signal:

$$K_k = \frac{V^{-1}}{P_k^{-1} + V^{-1} - \gamma} \qquad \text{equation (12)}$$

$$\hat{x}_{k+1} = \hat{x}_k + K_k(y_k - \hat{x}_k) \qquad \text{equation (13)}$$

$$P_{k+1} = \frac{1}{P_k^{-1} + V^{-1} - \gamma} + W \qquad \text{equation (14)}$$

In equations (12)-(14), the $\gamma$, V, and W variables are parameters that may be chosen in advance to give a desired performance. For example, at the development stage of a pulse oximeter 100, the $H_\infty$ filter may be hard-coded with certain inputs based on the pulse oximeter 100, the site of measurement, and/or the physiological data to be calculated. As the $H_\infty$ filter equations may have inputs that are pre-programmed and not dependent on noise statistics, the signal may be filtered without an exact signal model, and without a priori knowledge of noise statistics (e.g., the noise variances $S_w$ and $S_z$ required for the Kalman filter may not be required for a $H_\infty$ filter).

In one embodiment, the $H_\infty$ filter may be combined with other filtering techniques. For example, the γ, V, and W variables may also be varied adaptively according to a condition of the pulse oximeter 100, a type of sensor 114 used in the pulse oximeter 100, changes in noise conditions, and/or changes in the measured signal. The variables γ, V, and W, and other inputs of the $H_\infty$ filter or other filtering equations, may be stored in the memory 144 of the pulse oximeter 100 in the sensor 114 itself, or any other suitable component accessible by the digital filter 142. The filter variables γ, V, and W may also be altered depending upon user selection. For example, the user may prefer a faster response at the expense of decreased noise tolerance or a slower response with increased noise tolerance. A set of filter variables may be stored for each of these two example user modes. The user may also be able indirectly select the filter variable dependent upon the operating environment. For example, there may be a set of filter variables in the oximeter for the OR, General Care Floor, Transport, Sleep Lab, ICU, NICU, etc.

Furthermore, modifications to the filter variables may be made by the pulse oximeter 100 itself, based on previous measuring conditions. As the pulse oximeter 100 begins to detect the transmitted light and convert the light to an electrical signal (i.e., the pulse oximetry signal), the filter 142 (which may comprise algorithms similar to the $H_\infty$ filter algorithms previously discussed) may use the characteristics of the pulse oximetry signal to change the filter variables. For example, the filter 142, or a processor 122 coupled to the filter 142, may calculate the variance of the pulse oximetry signal over some period of time (e.g., over the last second). Further, the filter 142 and/or processor 122 may take a rolling average of noise variances over the duration of the measurement. In one embodiment, the $H_\infty$ inputs may be changed based on detected changes in noise sources or measurement errors. Thus, in accordance with the present techniques, a pulse oximetry signal may still be filtered with $H_\infty$ filter algorithms without using a priori knowledge of noise statistics. Furthermore, a digital filter 142 of the present techniques may also include methods of adapting an $H_\infty$ filter by changing $H_\infty$ filter inputs based on detected changes in noise characteristics.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A method of filtering a pulse oximetry signal, comprising: inputting the pulse oximetry signal into filtering algorithms, wherein the filtering algorithms comprise pre-programmed weighting matrices that depend on one or more of a characteristic of a sensor, a patient measurement site, or a type of physiological data to be collected, and wherein the filtering algorithms comprise $H_\infty$ filter algorithms adapted to filter the pulse oximetry signal.

2. The method of claim 1, comprising executing the filtering algorithms without a priori noise statistics.

3. The method of claim 2, comprising:
outputting a filtered pulse oximetry signal; and
estimating physiological data from the filtered pulse oximetry signal, wherein the worst possible estimation errors are minimized in estimating the physiological data.

4. The method of claim 1, comprising:
determining noise statistics from the pulse oximetry signal; and
updating the filtering algorithms based on the determined noise statistics.

5. The method of claim 1, wherein the physiological data comprises one or more of blood-oxygen saturation, pulse rate, and volume of blood pulsation in tissue.

6. A pulse oximetry system comprising:
a sensor configured to transmit light into and receive light from tissue, and further configured to output an analog signal based on the received light;
an analog-to-digital converter configured to digitize the analog signal; and
a digital filter configured to filter the digitized signal with $H_\infty$ filtering algorithms, wherein the filtering algorithms comprise pre-programmed weighting matrices that depend on one or more of a sensor characteristic, a patient measurement site, or a type of physiological data to be collected.

7. The pulse oximetry system of claim 6, comprising a memory component accessible by the digital filter, and wherein the $H_\infty$ filtering algorithms are stored in the memory component.

8. The pulse oximetry system of claim 7, wherein the memory component comprises weighting matrices, and wherein the digital filter uses the weighting matrices to filter the digitized signal with the $H_\infty$ filtering algorithms.

9. The pulse oximetry system of claim 6, wherein the digital filter is configured to use adaptive filtering algorithms to detect changes in the digital signal.

10. The pulse oximetry system of claim 9, wherein the $H_\infty$ filtering algorithms are substantially modifiable based on the detected changes in the digital signal.

11. The pulse oximetry system of claim 6, wherein the digital filter is configured to filter the digitized signal with the $H_\infty$ filtering algorithms when the digitized signal comprises noise that does not have a stationary zero-mean noise distribution.

12. The pulse oximetry system of claim 6, wherein the digital filter is configured to filter the digitized signal with the $H_\infty$ filtering algorithms when the digitized signal comprises noise that does not have a known variance.

13. The pulse oximetry system of claim 6, comprising a processor configured to calculate physiological data based on the filtered signal.

14. The pulse oximetry system of claim 13, wherein the physiological data comprises at least one of blood-oxygen saturation, pulse rate, or volume of blood pulsation in tissue.

15. A pulse oximetry monitor comprising:
a processor configured to determine whether a pulse oximetry system has a stationary zero-mean noise distribution, to access one or more stored filtering algorithms, to select an $H_\infty$ filtering algorithm from the one or more stored filtering algorithms when the pulse oximetry system is determined not to have a stationary zero-mean noise distribution, and to execute the $H_\infty$ filtering algorithm on a pulse oximetry signal to minimize a maximum error in the pulse oximetry signal.

16. The pulse oximetry monitor of claim 15, wherein the processor is configured to select and to execute a Kalman filtering algorithm when the pulse oximetry system is determined to have a stationary zero-mean noise distribution.

17. The pulse oximetry monitor of claim 15, wherein the processor is configured to use an adaptive filtering algorithm to detect changes in the pulse oximetry signal, and wherein the processor is configured to modify the selected $H_\infty$ filtering algorithm based on the detected changes.

18. The pulse oximetry monitor of claim 15, wherein the processor is configured to estimate physiological data based on a filtered pulse oximetry signal.

19. The pulse oximetry monitor of claim 15, wherein the processor is configured to select the $H_\infty$ filtering algorithm when the pulse oximetry signal is determined to comprise noise with a non-Gaussian distribution.

* * * * *